(12) United States Patent
Zhang et al.

(10) Patent No.: US 7,891,636 B2
(45) Date of Patent: Feb. 22, 2011

(54) SILICONE MOLD AND USE THEREOF (75) Inventors: Jun-Ying Zhang, Woodbury, MN (US); Mark J. Pellerite, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 712 days.

(21) Appl. No.: 11/845,465

(22) Filed: Aug. 27, 2007

(65) Prior Publication Data
US 2009/0061039 A1 Mar. 5, 2009

(51) Int. Cl.
B28B 7/38 (2006.01)

(52) U.S. Cl. ............ 249/134; 249/114.1; 249/115; 425/385; 428/447; 428/41.8; 106/38.22; 106/38.9; 427/133

(58) Field of Classification Search ........ 249/114.1, 249/115, 134, 135; 428/41.4, 41.8, 429, 428/447, 835.8, 846.3; 425/385; 427/133; 106/38.2, 38.22, 38.27, 38.9
See application file for complete search history.

(56) References Cited

U.S. PATENT DOCUMENTS

| 2,843,555 A | 7/1958 | Berridge |
| 3,159,662 A | 12/1964 | Ashby |
| 3,178,464 A | 4/1965 | Pierpoint |
| 3,220,972 A | 11/1965 | Lamoreaux |
| 3,250,808 A | 5/1966 | Moore, Jr. et al. |
| 3,313,773 A | 4/1967 | Lamoreaux |
| 3,410,886 A | 11/1968 | Joy |
| 3,470,255 A | 9/1969 | Kelly |
| 3,492,394 A * | 1/1970 | Heine .................. 264/338 |
| 3,567,755 A | 3/1971 | Seyfried et al. |
| 3,646,085 A * | 2/1972 | Bartlett ................ 556/419 |
| 3,671,007 A * | 6/1972 | Bailey et al. .......... 249/114.1 |
| 3,689,346 A | 9/1972 | Rowland |
| 3,715,334 A | 2/1973 | Karstedt |
| 3,775,452 A | 11/1973 | Karstedt |
| 3,810,874 A | 5/1974 | Mitsch et al. |
| 3,814,730 A | 6/1974 | Karstedt |
| 3,814,731 A | 6/1974 | Nitzsche et al. |
| 4,101,513 A | 7/1978 | Fox et al. |
| 4,276,252 A | 6/1981 | Kreis et al. |
| 4,288,345 A | 9/1981 | Ashby et al. |
| 4,313,988 A | 2/1982 | Koshar et al. |

(Continued)

FOREIGN PATENT DOCUMENTS

JP 04296336 10/1992

(Continued)

OTHER PUBLICATIONS

ARC: Xi et al., Optical thin-film material with low refractive index for broadband elimination of Fresnel reflection, Mar. 1, 2007, pp. 1-2.*
Uses of antisoiling coating, DuPont, pp. 1-2.*
Anti-adhering, anti-soiling coatings, pp. 1-2.*

(Continued)

Primary Examiner—Joseph S Del Sole
Assistant Examiner—Dimple Bodawala
(74) Attorney, Agent, or Firm—Kent S. Kokko (57) ABSTRACT A silicone mold comprising and oxidized, patterned surface and a layer of perfluoroether silane release agent is described. The mold enables $2^{nd}$ generation silicone molds to be replicated, i.e. silicone molds from silicone molds.

19 Claims, 2 Drawing Sheets

10μm

U.S. PATENT DOCUMENTS

| | | | |
|---|---|---|---|
| 4,510,094 A | | 4/1985 | Drahnak |
| 4,530,879 A | | 7/1985 | Drahnak |
| 4,582,885 A | | 4/1986 | Barber |
| 4,603,215 A | | 7/1986 | Chandra et al. |
| 4,640,939 A | | 2/1987 | Cavezzan et al. |
| 4,670,531 A | | 6/1987 | Eckberg |
| 4,677,137 A | | 6/1987 | Bany et al. |
| 4,699,813 A | | 10/1987 | Cavezzan |
| 4,705,765 A | | 11/1987 | Lewis |
| 4,712,092 A | | 12/1987 | Boldridge, Jr. et al. |
| 4,865,954 A | | 9/1989 | Hagiwara et al. |
| 4,916,169 A | | 4/1990 | Boardman et al. |
| 4,946,369 A | * | 8/1990 | Beck et al. ............... 427/133 |
| 5,089,536 A | | 2/1992 | Palazzotto |
| 5,091,483 A | | 2/1992 | Mazurek et al. |
| 5,183,597 A | | 2/1993 | Lu |
| 5,286,815 A | | 2/1994 | Leir et al. |
| 5,306,758 A | | 4/1994 | Pellerite |
| 5,316,716 A | | 5/1994 | Sato et al. |
| 5,409,773 A | | 4/1995 | Kessel et al. |
| 5,804,674 A | | 9/1998 | Yamana et al. |
| 5,851,674 A | | 12/1998 | Pellerite et al. |
| 5,861,113 A | * | 1/1999 | Choquette et al. ......... 264/1.24 |
| 5,932,150 A | | 8/1999 | Lacey |
| 6,096,247 A | | 8/2000 | Ulsh et al. |
| 6,204,350 B1 | | 3/2001 | Liu et al. |
| 6,277,485 B1 | | 8/2001 | Invie et al. |
| 6,376,065 B1 | | 4/2002 | Korba et al. |
| 6,376,569 B1 | | 4/2002 | Oxman et al. |
| 6,403,382 B1 | | 6/2002 | Zhu et al. |
| 6,656,258 B2 | * | 12/2003 | Elsbernd et al. ........... 106/287.1 |
| 6,673,287 B2 | * | 1/2004 | Breen et al. ................ 264/83 |
| 6,737,170 B2 | | 5/2004 | Fitch et al. |
| 6,743,516 B2 | | 6/2004 | Murphy et al. |
| 6,783,719 B2 | | 8/2004 | Robinson et al. |
| 6,788,463 B2 | | 9/2004 | Merrill et al. |
| 6,860,956 B2 | * | 3/2005 | Bao et al. ................ 156/232 |
| 6,974,549 B2 | * | 12/2005 | Ohgaki ................ 216/51 |
| 6,977,057 B2 | | 12/2005 | Reitz et al. |
| 7,014,799 B2 | | 3/2006 | Yang et al. |
| 7,057,832 B2 | | 6/2006 | Wu et al. |
| 7,173,778 B2 | | 2/2007 | Jing et al. |
| 7,294,731 B1 | * | 11/2007 | Flynn et al. ............... 556/427 |
| 2001/0044021 A1 | * | 11/2001 | Ogawa et al. ............... 428/333 |
| 2002/0090515 A1 | * | 7/2002 | Pellerite et al. ............. 428/406 |
| 2002/0190416 A1 | * | 12/2002 | Birch et al. ............... 264/85 |
| 2003/0175551 A1 | * | 9/2003 | Smith et al. ............... 428/690 |
| 2004/0157063 A1 | * | 8/2004 | Takahashi et al. ........... 428/447 |
| 2004/0202865 A1 | * | 10/2004 | Homola et al. .............. 428/421 |
| 2005/0048288 A1 | | 3/2005 | Flynn et al. |
| 2005/0089694 A1 | * | 4/2005 | Moffatt et al. .............. 428/429 |
| 2005/0089696 A1 | * | 4/2005 | Bosshammer ................ 428/447 |
| 2006/0012079 A1 | | 1/2006 | Jung et al. |
| 2006/0046069 A1 | * | 3/2006 | Jung et al. .................. 428/429 |
| 2006/0172901 A1 | | 8/2006 | Kubota et al. |
| 2007/0269747 A1 | * | 11/2007 | Bahadur et al. ............. 430/319 |
| 2008/0145525 A1 | * | 6/2008 | Guo et al. ................... 427/133 |
| 2008/0203271 A1 | * | 8/2008 | Okinaka et al. .......... 249/114.1 |
| 2008/0203620 A1 | * | 8/2008 | Okinaka et al. ............. 264/483 |
| 2009/0068475 A1 | * | 3/2009 | Bosshammer ................ 428/447 |
| 2010/0055474 A1 | * | 3/2010 | Bachon et al. .............. 428/429 |

FOREIGN PATENT DOCUMENTS

| | | | |
|---|---|---|---|
| JP | 2007106819 | | 4/2007 |
| JP | 2008137306 | | 6/2008 |
| WO | WO 9937720 A1 | * | 7/1999 |
| WO | WO 01/30931 A1 | | 5/2001 |
| WO | WO 01/68940 A1 | | 9/2001 |
| WO | WO 2006107082 A2 | * | 10/2006 |
| WO | WO 2008/112400 | | 9/2008 |

OTHER PUBLICATIONS

Lee et al., Antiadhesion Surface Treatments of Molds for High Resolution Unconventional Lithography, Advanced material, 2006,18, pp. 3115-3119.*

"Encyclopedia of Polymer Science and Technology", (1968), p. 651, vol. 8, John Wiley & Sons, Inc.

"Silicones" Encyclopedia of Polymer Science and Engineering, (1989), pp. 234-243, 252, vol. 15, John Wiley & Sons, Inc.

Bhattacharya et al., "Studies on Surface Wettability of Poly(Dimethyl) Siloxane (PDMS) and Glass Under Oxygen-Plasma Treatment and Correlation With Bond Strength", Journal of Microelectromechanical Systems, (Jun. 2005), pp. 590-597, vol. 14, No. 3, IEEE.

Blum et al., "Principles of Electroplating and Electroforming (electrotyping)", (1949), 3$^{rd}$ Edition, McGraw-Hill Book Company.

Chua et al., "Spontaneous Formation of Complex and Ordered Structures on Oxygen-Plasma-Treated Elastomeric Polydimethylsiloxane", Applied Physics Letters, (Feb. 2000), pp. 721-723, vol. 76, No. 6, American Institute of Physics.

Clarson, et al., "Siloxane Polymers", (1993), PTR Prentice Hall, Inc.

Crivello et al., "Cationic Photopolymerization of Ambifunctional Monomers", Macromol. Symp. (1995), pp. 79-89, vol. 95, Hüthig & Wepf Verlag, Zug.

Davies et al., "Application of Precision Diamond Machining to the Manufacture of Micro-Photonic Components", Proc. of SPIE, (2003), pp. 94-108, vol. 5183.

Kley, "Continuous Profile Writing by Electron and Optical Lithography", Microelectronic Engineering, (1997), pp. 261-298, vol. 34, Elsevier Science B.V.

Kumar, "Features of Gold Having Micrometer to Centimeter Dimensions Can Be Formed Through a Combination of Stamping With an Elastomeric Stamp and an Alkanethiol "Ink" Followed by Chemical Etching", Appl. Phys. Lett. (1993), pp. 2002-2004, vol. 14, No. 4, American Institute of Physics.

Noll, "Chemistry and Technology of Silicones", (1968), Academic Press, Inc.

Pappas, "Photopolymerizable Silicone Monomers, Oligomers, and Resins", Radiation Curing Science and Technology, (1992), pp. 200-214, Plenum Press, New York.

Park et al., "Fabrication of PDMS Replica Using Nano Replication Printing Process and Vacuum Pressure-Difference Technique", INSM 2004, KAIST, Daejeon, Korea, (2004), pp. 1-3.

Plueddemann et al., "Epoxyorganosiloxanes", M. Am. Chem. Soc., (1959), pp. 2632-2635, vol. 81.

Pocius et al., "Adhesion at Polymer Interfaces and Pressure Sensitive Adhesive Tapes", Plastics Engineering, (1997), pp. 31-97, vol. 53, No. 12.

Quake et al., "From Micro- to Nanofabrication With Soft Materials". Science, (2000), pp. 1536-1540, vol. 290.

Schaefer et al., "Surface Replicas for Use in the Electron Microscope", Journal of Applied Physics, (1942), pp. 427-433, vol. 13.

Tomanek, "Silicone & Industry, A Compendium for Practical Use, Instruction and Reference", (1993), Wacher-Chemie, Munich.

Vasilets et al., "Improvement of the Micro-Wear Resistance of Silicone by Vacuum Ultraviolet Irradiation", Polymer, (1997), pp. 2875-2881, vol. 39, No. 13, Elsevier Science Ltd.

Wilkinson, "Silicones", Comprehensive Organometallic Chemistry, (1982), pp. 329-330, vol. 2, Pergamon Press, Ltd.

Xia et al., "Soft Lithography", Angew. Chem. Int. Ed., (1998), pp. 550-575, vol. 37, WILEY-VCH Verlag GmbH, D-69451 Weinheim.

Yan et al., "$CF_4$ Plasma Treatment of Poly(dimethylsiloxane): Effect of Fillers and Its Application to High-Aspect-Ratio UV Embossing", Langmuir, (2005), pp. 8905-8912, vol. 21, No. 19, American Chemical Society.

Zhao et al., "Soft Lithographic Methods for Nano-Fabrication", J. Mater. Chem., (1997), pp. 1069-1074, vol. 7, No. 7.

PCT International Search Report, PCT/US2008/073450.

\* cited by examiner

*Fig. 4*

US 7,891,636 B2

SILICONE MOLD AND USE THEREOF

FIELD OF THE INVENTION

This invention relates to silicone molds and the replication of surfaces bearing microstructures and/or nanostructures, in the production of shaped articles such as retroreflecting cube-corner sheeting, Fresnel lens elements, diffraction gratings, video discs, photonic crystal structures, microfluidic channels, and ophthalmic lenses, and to a process for the preparation of the mold.

BACKGROUND

There is an interest in commercial and industrial applications to reduce the size of articles and devices, such as in electronics where devices have been made smaller and smaller. Micro- and nanostructured devices, for example, can be used in articles such as flat panel displays, chemical sensors, and bioabsorption substrates. Microstructured articles have found commercial utility in, for example, electroluminescent devices, field emission cathodes for display devices, microfluidic films, and patterned electronic components and circuits.

Various mold-based micro and nano-replication technologies have been reported, such as nano-embossing lithography, nano-imprint lithography, ultraviolet-nano-imprint lithography, and step-and-flash imprint lithography. In the nanoreplication process, replica quality can be negatively affected by interfacial phenomena such as wettability and adhesion between the mold and the replicated polymeric patterns. Such effects are particularly important for nanoscale features, due to the high surface to volume ratio of those features. In nanoreplication applications, where the pattern sizes of the mold are very small-on the order of micrometers to nanometers-conventional coating technology cannot be applied because a thick release layer on the mold can change the feature dimensions of the pattern.

SUMMARY

The present disclosure provides a silicone mold comprising an oxidized, three-dimensionally-patterned surface, and a layer of perfluoroether silane release agent on the patterned surface. Preferably the layer of release agent comprises a self-assembled monolayer on the oxidized, patterned surface of the mold. The present invention overcomes problems in the art by providing a mold that may be used repeatedly in casting silicone replica molds from the silicone master mold with little or no degradation in fidelity to the master.

In another embodiment, the present disclosure provides a method of replication comprising providing the silicone mold ("$1^{st}$ generation negative mold") comprising an oxidized, patterned surface, and a layer of perfluoroether silane release agent on the patterned surface, adding an silicone resin (an uncured silicone) in contact with the patterned surface of said mold; curing the silicone resin, and separating the cured silicone resin from the mold to produce a $2^{nd}$ generation daughter mold. It will be understood that the first generation negative mold has a pattern which is the negative of the original master mold (prepared, for example, by photolithographic techniques), while the $2^{nd}$ generation daughter mold is the negative of the $1^{st}$ generation negative mold, or identical to the master mold.

In another embodiment, the present disclosure provides a method of preparing a $1^{st}$ generation negative mold comprising the steps of providing a master mold, contacting the master mold with a curable silicone resin, curing the curable silicone resin, removing the cured silicone mold having a three-dimensional pattern on the surface thereof from the master mold, plasma treating the patterned surface; and contacting the patterned surface with a release agent to produce a $1^{st}$ generation negative mold, which may be used to produce shaped articles such as $2^{nd}$ generation daughter molds.

Curable silicone resins, such as polydimethylsiloxane (PDMS)-based polymers have been recently used in nano- and micro-molding due to their durability, chemical inertness, and low surface energy of the materials, combined with inexpensive and easy processing. However, the high surface hydrophobicity of silicone often prevents successful molding of high-aspect-ratio structures without the use of a specialized pressure or vacuum environment, which may cause structural deformation of the silicone mold. To address this issue, efforts have been made to transform the hydrophobic silicone surface to a hydrophilic $SiO_x$ surface by oxygen plasma, corona discharge, and UV/ozone treatments. However, these types of surface modification often promote excessively strong adhesion between the replica and the mold, increasing the difficulty of the demolding step in the micromolding process.

Many polymers, such as acrylate polymers, epoxies, and polyurethanes can be directly replicated from a silicone mold without any surface treatment, since the silicone has low surface energy and itself serves as a release agent during the replication process. However, if one would like to make a silicone replica mold from the silicone master mold, one method is to metallize the silicone mold. For example, S. H. Park, et al. "Fabrication Of PDMS Replica Using Nano Replication Printing Process And Vacuum Pressure-Difference Technique", where a thin gold (30 nm) layer was deposited on the silicone master pattern prior to the application of silicone for replication, in order to prevent bonding of the master and the silicone replica. In this approach each replica requires coating gold onto the silicone master, which increases process time and makes the process more expensive.

It is desirable to make $2^{nd}$ generation daughter silicone molds from a first generation silicone negative because is enable the preparation of multiple copies of the master mold that may be used in production of shaped articles without relying on the master, and may be tiled to more efficiently produce such shaped articles.

As used herein, the articles "a", "an", and "the" are used interchangeably with "at least one" to mean one or more of the elements being described.

"etch mask" refers to a structure that is held in proximity to or in contact with the substrate so as to allow or to prevent exposure of regions of the substrate to optical or etchant beams.

"etch resist" refers to a layer or layers of material that is placed on the substrate and can be patterned to form a resist pattern, which, under the etching conditions used, etches more slowly than the substrate.

"resist" refers to a layer or layers of material that is placed on the substrate to selectively allow an etching agent to pass through in a patterned manner, as in photolithographic processes.

"microstructure" or "microstructures" refer to structures that range from about 0.1 microns to about 1000 microns in their longest dimension. In this application, the ranges of nanostructures and microstructures may overlap.

"nano", as in "nanofeature" or "nanostructure" refer to pattern features or elements that range from about 1 nm to about 1000 nm in their longest dimension. The nanostructure of any article of this application are smaller than the microscale structures generated on the article;

"pattern" or "patterns" refer to a configuration or configurations that can include regular arrays or random arrays of features or structures or a combination of both; and "resist" refers to a layer or layers of material that is placed on the substrate to selectively allow an etching agent to pass through in a patterned manner, as in photolithographic processes.

"Alkyl" means a linear or branched, cyclic or acyclic, saturated monovalent hydrocarbon radical having from one to about twelve carbon atoms, e.g., methyl, ethyl, 1-propyl, 2-propyl, pentyl, and the like.

"Alkylene" means a linear saturated divalent hydrocarbon radical having from one to about twelve carbon atoms or a branched saturated divalent hydrocarbon radical having from three to about twelve carbon atoms, e.g., methylene, ethylene, propylene, 2-methylpropylene, pentylene, hexylene, and the like.

"Alkoxy" means an alkyl having a terminal oxygen atom, e.g. $CH_3$—O—, $C_2H_5$—O—, and the like.

"Aralkylene" means an alkylene radical defined above with an aromatic group attached to the alkylene radical, e.g., benzyl, 1-naphthylethyl, and the like.

"Arylene" means a divalent unsaturated aromatic carbocyclic radicals having one to three rings, multiple fused rings, or combinations thereof. That is, an arylene is a divalent radical of a carbocyclic aromatic compound.

"Cured chemical composition" means that the chemical composition is dried or solvent has evaporated from the chemical composition from ambient temperature or higher until dryness. The composition may further be crosslinked as result of siloxane bonds formed between the urethane compounds.

"Oxyalkoxy" has essentially the meaning given above for alkoxy except that one or more oxygen atoms may be present in the alkyl chain and the total number of carbon atoms present may be up to 50, e.g. $CH_3CH_2OCH_2CH_2O$—, $C_4H_9OCH_2CH_2OCH_2CH_2O$—, $CH_3O(CH_2CH_2O)_{1-100}$—, and the like.

"Oxyalkyl" has essentially the meaning given above for alkyl except that one or more oxygen heteroatoms may be present in the alkyl chain, these heteroatoms being separated from each other by at least one carbon, e.g., $CH_3CH_2OCH_2CH_2$—, $CH_3CH_2OCH_2CH_2OCH(CH_3)CH_2$—, $C_4H_9CH_2OCH_2CH_2$—, and the like.

"Oxyalkylene" has essentially the meaning given above for alkylene except that one or more oxygen heteroatoms may be present in the alkylene chain, these heteroatoms being separated from each other by at least one carbon, e.g., —$CH_2OCH_2O$—, —$CH_2CH_2OCH_2CH_2$—, —$CH_2CH_2OCH_2CH_2CH_2$—, and the like.

"Halo" means fluoro, chloro, bromo, or iodo, preferably fluoro and chloro.

"Perfluorinated group" means an organic group wherein all or essentially all of the carbon bonded hydrogen atoms are replaced with fluorine atoms, e.g. perfluoroalkyl, perfluorooxyalkyl, and the like.

"Perfluoroalkyl" has essentially the meaning given above for "alkyl" except that all or essentially all of the hydrogen atoms of the alkyl radical are replaced by fluorine atoms and the number of carbon atoms is from 1 to about 12, e.g. perfluoropropyl, perfluorobutyl, perfluorooctyl, and the like.

"Perfluoroalkylene" has essentially the meaning given above for "alkylene" except that all or essentially all of the hydrogen atoms of the alkylene radical are replaced by fluorine atoms, e.g., perfluoropropylene, perfluorobutylene, perfluorooctylene, and the like.

"Perfluorooxyalkyl" has essentially the meaning given above for "oxyalkyl" except that all or essentially all of the hydrogen atoms of the oxyalkyl radical are replaced by fluorine atoms and the number of carbon atoms is from 3 to about 100, e.g. $CF_3CF_2OCF_2CF_2$—, $CF_3CF_2O(CF_2CF_2O)_3CF_2CF_2$—, $C_3F_7O(CF(CF_3)CF_2O)_sCF(CF_3)CF_2$—, where s is (for example) from about 1 to about 50, and the like.

"Perfluorooxyalkylene" has essentially the meaning given above for "oxyalkylene" except that all or essentially all of the hydrogen atoms of the oxyalkylene radical are replaced by fluorine atoms, and the number of carbon atoms is from 3 to about 100, e.g., —$CF_2OCF_2$—, or —$[CF_2—CF_2—O]_b$—$[CF(CF_3)—CF_2—O]_c$—; wherein b and c are (for example) integers of 1 to 50. "Perfluoroether" is a group having at least one perfluorooxyalkylene group; e.g perfluoroethers and perfluoropolyethers.

"Perfluoropolyether" is a group having at least two perfluorooxyalkylene groups.

DETAILED DESCRIPTION

The present disclosure provides a silicone mold comprising an oxidized, patterned surface, and a layer of perfluoroether silane release agent on the patterned surface, said release agent is of the formula:

$$R_f—[—R^1—Si(Y)_{3-x}(R^2)_x]_y \quad (I)$$

wherein:

$R_f$ is a monovalent or divalent perfluoroether group;

$R^1$ is a divalent alkylene group, arylene group, or combinations thereof, optionally containing one or more heteroatoms or functional groups and optionally substituted with halides, and preferably containing about 2 to about 16 carbon atoms;

$R^2$ is a lower alkyl group, Y is a hydrolysable group, such as an alkoxy, acyloxy or halo group;

x is 0 or 1; and y is 1 or 2.

The perfluoroether group ($R_f$) can include linear, branched, and/or cyclic structures, that may be saturated or unsaturated, and substituted with one or more oxygen atoms. It is a perfluorinated group (i.e., all C—H bonds are replaced by C—F bonds). More preferably, it includes perfluorinated repeating units selected from the group of —$(CnF_{2n})$—, —$(C_nF_{2n}O)$—, —$(CF(Z))$—, —$(CF(Z)O)$—, —$(CF(Z)C_nF_{2n}O)$—, —$(C_nF_{2n}CF(Z)O)$—, —$(CF_2CF(Z)O)$—, and combinations thereof. In these repeating units Z is a perfluoroalkyl group, an oxygen-substituted perfluoroalkyl group, a perfluoroalkoxy group, or an oxygen-substituted perfluoroalkoxy group, all of which can be linear, branched, or cyclic, and preferably have about 1 to about 9 carbon atoms and 0 to about 4 oxygen atoms, and n is 1 or more, and preferably about 1 to about 6.

Examples of perfluoroethers containing polymeric moieties made of these repeating units are disclosed in U.S. Pat. No. 5,306,758 (Pellerite). Preferably the number of repeat units in the perfluoroether group ($R_f$) is sufficient to form a compound having a number average molecular weight of at least about 500, and more preferably, sufficient to form a perfluoroether group having a number average molecular weight of at least about 1000. For the monovalent perfluoroether group (wherein y is 1 in Formula I above), the terminal groups can be $(C_nF_{2n+1})$—, $(C_nF_{2n+1}O)$—, $(X'C_nF_{2n}O)$—, or $(X'C_nF_{2+1})$— wherein X' is H, Cl, or Br, and n is an integer of 1 to 6. Preferably, these terminal groups are perfluorinated.

Preferred approximate average structures for a divalent perfluoroether group include units of —$CF_2O(CF_2O)_a(C_2F_4O)_bCF_2$—, —$CF(CF_3)(OCF_2CF(CF_3))_cO(CF_2)_nO(CF(CF_3)CF_2O)_c$—, where n is 1-6; —$CF_2O(C_2F_4O)_bCF_2$—, and —$(CF_2)_3O(C_4F_8O)_d(CF_2)_3$—, wherein an average value for a, b, c and d is 0 to about 50, all of a, b, c and d cannot be 0 in the same group, and a+b+c+d is at least 1, preferably at least 2, and most preferably 10 to 50, and n is 1 to 6. It will be understood that the value of the "c" subscript in "$(OCF_2CF(CF_3))_c$" is selected independently from the value of the "c" subscript in "$(CF(CF_3)CF_2O)_c$".

Of these, particularly preferred approximate average structures are —$CF_2O(CF_2O)_a(C_2F_4O)_bCF_2$—, —$CF_2O(C_2F_4O)_bCF_2$—, and —$CF(CF_3)(OCF_2CF(CF_3))_cO(CF_2)_nO(CF(CF_3)CF_2O)_cCF(CF_3)$—, where a, b, c and d is 0 to about 50, all of a, b, c and d cannot be 0 in the same group, and a+b+c+d is at least 1, preferably at least 2, and most preferably 10 to 50.

Particularly preferred approximate average structures for a monovalent perfluoroether group include $C_3F_7O(CF(CF_3)CF_2O)_cCF(CF_3)$— and $CF_3O(C_2F_4O)_bCF_2$— wherein an average value for b and c is 1 to about 50, preferably at least 2, and most preferably 10 to 50. As synthesized, these compounds typically include a mixture of polymers. The approximate average structure is the approximate average of the mixture of polymers and the number may be non-integral.

Compounds of formula 1 suitable for use in making a release agent useful in the present invention have a molecular weight (number average) of at least about 500, and preferably, at least about 1000. Typically, they are no greater than about 5000, but this is typically limited by availability, viscosity, and ease of cure, and preferably, no greater than about 3000, depending upon the viscosity and cure time characteristics desired.

Examples of preferred fluorinated silanes include, but are not limited to, the following approximate average structures: $XCF_2O(CF_2O)_a(C_2F_4O)_bCF_2X$, $C_3F_7O(CF(CF_3)CF_2O)_cCF(CF_3)X$, $XCF(CF_3)(OCF_2CF(CF_3))_cO(CF_2)_nO(CF(CF_3)CF_2O)_cCF(CF_3)X$, $XCF_2O(C_2F_4O)_bCF_2X$, and $CF_3O(C_2F_4O)_bCF_2X$, $X(CF_2)_3O(C_4F_8O)_d(CF_2)_3X$, wherein —X is —$R^1$—$Si(Y)_{3-x}(R^2)_x$ as defined above in Formula I or a nonsilane-containing terminal group as defined above $(C_nF_{2n+1})$—, $(C_nF_{2n+1})$—, $(X'C_nF_{2n}O)$—, or $(X'C_nF_{2n+1}O)$— wherein X' is H, Cl, or Br), with the proviso that at least one X group per molecule is a silane, where a, b, c and d is 0 to about 50, all of a, b, c and d cannot be 0 in the same group, and a+b+c+d is at least 1, preferably at least 2, and most preferably 10 to 50.

In some embodiments, each silane $R^1$ group preferably includes nitrogen. More preferably, at least one X group per molecule is $C(O)NH(CH_2)_3Si(OR)_3$ (wherein $R^1$ is methyl, ethyl, or mixtures thereof), and the other X group if not a silane is —$OCF_3$ or —$OC_3F_7$. The values of a, b, c and d in these approximate average structures can vary, as long as the material has a number average molecular weight of at least about 500.

In certain embodiments, an average value of a, b, c and d are each within a range of about 1 to about 50, and the sum of a, b, c and d is within a range of about 10 to about 50. As these are polymeric materials, such compounds exist as mixtures upon synthesis, which are suitable for use. These mixtures may also contain perfluoroether chains bearing no functional groups (inert fluids) or more than two terminal groups (branched structures) as a consequence of the methods used in their synthesis. Typically, mixtures of polymeric materials containing less than about 10% by weight of non-functionalized polymers (e.g., those without silane groups, for example) can be used. Furthermore, mixtures of any of the individually listed compounds of formula I can be used.

Perfluoropolyether compounds can be obtained by oligomerization of hexafluoropropylene oxide (HFPO) which results in a perfluoropolyether carbonyl fluoride as described in U.S. Pat. No. 3,250,808 (Moore et al.), incorporated herein by reference. This carbonyl fluoride may be converted into an acid, acid salt, ester, amide or alcohol by reactions well known to those skilled in the art. The carbonyl fluoride or acid, ester or alcohol derived therefrom may then be reacted further to introduce the desired groups according to known procedures.

The compounds of formula I can be synthesized using standard techniques. For example, commercially available or readily synthesized perfluoropolyether esters can be combined with a functionalized alkoxysilane, such as a 3-aminopropylalkoxysilane, according to U.S. Pat. No. 3,810,874 (Mitsch et al.). Modifications of this method are described in the Examples. Such materials may or may not need to be purified before use in a release composition.

It will be evident to one skilled in the art that a mixture of perfluoroethers according to formula (I) may be used to prepare the fluorinated polyether compound of the fluorochemical composition. Generally, the method of making the perfluoroether according to formula (I) for the present invention will result in a mixture of perfluoroethers that have different molecular weights and are free of (1) fluorinated polyether compounds having a perfluorinated polyether moiety having a molecular weight of less than 750 g/mol and (2) fluorinated polyether compounds having a perfluoropolyether moiety having a molecular weight greater than 10,000 g/mol.

The use of perfluoropolyethers corresponding to molecular weights greater than about 5,000 g/mol can induce processing problems. These problems are typically due to the fact that the higher molecular weight materials lead to insolubility concerns, as well as in difficulty in application methods such as CVD coating due to the low vapor pressure of these higher molecular weight compounds. Additionally, the presence of higher molecular weight perfluoroether compound may have considerable impact on the efficiency of the purification process of materials via fractionation.

The fluorochemical composition are desirably free of or substantially free of perfluoropolyether moieties having a molecular weight of less than 500 g/mol and those moieties having a molecular weight greater than 5000 g/mol. By the term "substantially free of" is meant that the particular perfluoropolyether moieties outside the molecular weight range are present in amounts of not more than 10% by weight, preferably not more than 5% by weight and based on the total weight of perfluoropolyether moieties in the composition. Compositions that are free of or substantially free of these moieties are preferred because of their beneficial environmental properties and their processability in the further reaction steps.

The divalent $R^1$ group of Formula I can include linear, branched, or cyclic structures, that may be saturated or unsaturated. The $R^1$ group can contain one or more heteroatoms (e.g., oxygen, nitrogen, or sulfur) or functional groups (e.g., carbonyl, amido, or sulfonamido). It can also be substituted with halogen atoms, preferably, fluorine atoms, although this is less desirable, as this might lead to instability of the compound. Preferably, the divalent $R^1$ group is a hydrocarbon group, preferably, a linear hydrocarbon group, optionally containing heteroatoms or functional groups, and more preferably, containing at least one functional group. Examples of $R^1$ groups include —C(O)NH(CH$_2$)$_3$—, —CH$_2$—O (CH$_2$)$_3$—, and —(C$_n$H$_{2n}$)—, wherein n is about 2 to about 6. A preferred $R^1$ group is —C(O)NH(CH$_2$)$_3$—.

Although the inventors do not wish to be bound by theory, compounds of the above Formula I are believed to undergo reaction with the oxidized silicone surface to form a siloxane coating that has a strong interaction with the oxidized silicone surface, such as through the formation of covalent bonds. In this context, "siloxane" refers to —Si—O—Si— bonds to which are attached perfluoroether segments (such as the $R_f$ groups in Formula I herein), preferably, perfluoropolyether segments, bonded to the silicon atoms through organic linking groups optionally containing heteroatoms or functional groups (such as the $R^1$ groups in formula I herein). In a cured coating (or an at least partially cured coating), the perfluoroether segments preferably have a number average molecular weight of at least about 500. In particularly preferred embodiments, the $R^1$ groups include nitrogen atoms (as in an amido group), and the ratio of fluorine atoms to nitrogen atoms in the coating is within a range of about 25 to about 150. A coating prepared from a coating composition that includes compounds of formula I can also include unreacted or uncondensed silanol groups.

The silicone mold comprises a cured silicone selected from a condensation curable silicone, an addition-curable (or hydrosilylation curable) silicone, a free radical-cure silicone, or a cationic-curable silicone. Curable silicones can provide long-term durability and are useful over a wide range of temperature, humidity and environmental conditions, and can be used effectively to bond the laminated body of the invention. In some embodiments, the curable silicones may be photocurable silicones, including UV and visible light curable silicones. In some embodiments, the curable silicone may further comprise a reinforcing agent such as a silica, quartz, and/or MQ resin, which reinforces the cured silicone. Such a reinforcing agent may be added in amounts up to 75 wt. % of the curable silicone composition.

General references regarding curable silicone polymers include Kirk-Othmer Encyclopedia of Polymer Science and Engineering, $2^{nd}$ edition, Wiley-Interscience Pub., 1989, volume 15, pp. 235-243; Comprehensive Organometallic Chemistry, Ed. Geoffrey Wilkinson, Vol. 2, Chapter 9.3, F. O. Stark, J. R. Falender, A. P. Wright, pp. 329-330, Pergamon Press: New York, 1982; Silicones and Industry: A Compendium for Practical Use, Instruction, and Reference, A. Tomanek, Carl Hanser: Wacher-Chemie: Munich, 1993; Siloxane Polymers, S. J. Clarson, Prentice Hall: Englewood Cliffs, N. J., 1993; and Chemistry and Technology of Silicones, W. Noll, Verlag Chemie: Weinheim, 1960.

The curable silicone can be an addition-cure or hydrosilylation cure silicone comprising an ethylenically unsaturated (e.g. alkenyl or (meth)acryloyl) functional silicone base polymer, a hydride functional cross-linking or chain extending agent (e.g., SiH), and a hydrosilylation catalyst. The silicone base polymer has ethylenically unsaturated (e.g., vinyl, propenyl, higher alkenyl, (meth)acryloyl, etc.) groups which may be present at the ends of the polymer (terminal) and/or pendent along the polymer chain. Preferably the ethylenically unsaturated groups are vinyl or higher alkenyl groups. It may be desirable for a reinforcing agent to be included such as, for example, a silica, quartz, and/or MQ resin containing alkenyl or SiH functional groups. The hydrosilylation catalyst may be a Group VIII metal or metal complex or supported metal catalyst, but is typically a noble metal catalyst containing, for example, Pt or Rh.

Addition-cured silicones (e.g., hydrosilylation cured silicones) are generally considered to be of higher quality and are more dimensionally stable than condensation-cured silicones. Unlike condensation-cured silicones, addition-cured silicones, e.g., hydrosilylation-cured silicones do not produce potentially detrimental byproducts during curing. Such silicones differ from condensation-cured silicones in that the hydrosilylation-cured composition typically contains 1) an ethylenically polyunsaturated silicone polymer or oligomer; 2) a "hydrosilane" component containing two or more silane (Si—H) bonds; and 3) a hydrosilylation catalyst such as a platinum catalyst. By "ethylenically polyunsaturated" it is meant a compound or component having a plurality of ethylenically unsaturated groups, such as a plurality of vinyl groups and (meth)acryloyl groups. The ethylenically unsaturated groups and the Si—H groups may be terminal or pendent. In some embodiments, the silicone may have both Si—H bonds and vinyl groups.

A particularly preferred addition-cured silicone is formed by reacting (1) a multiply-ethylenically unsaturated group-containing organopolysiloxane with (2) an organopolysiloxane containing a multiplicity of SiH bonds per molecule (hereinafter "organohydropolysiloxane"). This reaction is typically facilitated by the presence of (3) a platinum-containing catalyst.

The curable silicone composition can be prepared by combining (e.g., mixing together) the ethylenically polyunsaturated organopolysiloxane, the organohydropolysiloxane, and the hydrosilylation catalyst. In one embodiment, the components are pre-mixed into preferably two parts prior to use. For example, part "A" may contain the vinyl-containing organopolysiloxane, and the catalyst, while part "B" may contain the organohydropolysiloxane and optionally vinyl-containing organopolysiloxane. In another embodiment, the components are provided in one part and further contain an ingredient (e.g., a catalyst inhibitor) that inhibits the cure reaction.

Numerous patents teach the use of various complexes of cobalt, rhodium, nickel, palladium, or platinum as catalysts for accelerating the thermally-activated addition reaction (hydrosilylation) between a compound containing silicon-bonded hydrogen and a compound containing aliphatic unsaturation. For example, U.S. Pat. No. 4,288,345 (Ashby et al) discloses as a catalyst for hydrosilylation reactions a platinum-siloxane complex. Additional platinum-siloxane complexes are disclosed as catalysts for hydrosilylation reactions in U.S. Pat. Nos. 3,715,334, 3,775,452, and 3,814,730 (Karstedt et al). U.S. Pat. No. 3,470,225 (Knorre et al) discloses production of organic silicon compounds by addition of a compound containing silicon-bonded hydrogen to organic compounds containing at least one non-aromatic double or triple carbon-to-carbon bond using a platinum compound of the empirical formula PtX$_2$(RCOCR'COR")$_2$ wherein X is halogen, R is alkyl, R' is hydrogen or alkyl, and R" is alkyl or alkoxy. The catalysts disclosed in the foregoing patents are characterized by their high catalytic activity.

Other platinum complexes for accelerating the aforementioned thermally-activated addition reaction include: a platinacyclobutane complex having the formula $(PtCl_2C_3H_6)_2$ (U.S. Pat. No. 3,159,662, Ashby); a complex of a platinous salt and an olefin (U.S. Pat. No. 3,178,464, Pierpoint); a platinum-containing complex prepared by reacting chloroplatinic acid with an alcohol, ether, aldehyde, or mixtures thereof (U.S. Pat. No. 3,220,972, Lamoreaux); a platinum compound selected from trimethylplatinum iodide and hexamethyldiplatinum (U.S. Pat. No. 3,313,773, Lamoreaux); a hydrocarbyl or halohydrocarbyl nitrile-platinum (II) halide complex (U.S. Pat. No. 3,410,886, Joy); a hexamethyl-dipyridine-diplatinum iodide (U.S. Pat. No. 3,567,755, Seyfried et al); a platinum curing catalyst obtained from the reaction of chloroplatinic acid and a ketone having up to 15 carbon atoms (U.S. Pat. No. 3,814,731, Nitzsche et al); a platinum compound having the general formula $(R')PtX_2$ where R' is a cyclic hydrocarbon radical or substituted cyclic hydrocarbon radical having two aliphatic carbon-carbon double bonds, and X is a halogen or alkyl radical (U.S. Pat. No. 4,276,252, Kreis et al); platinum alkyne complexes (U.S. Pat. No. 4,603,215, Chandra et al.); platinum alkenylcyclohexene complexes (U.S. Pat. No. 4,699,813, Cavezzan); and a colloidal hydrosilylation catalyst provided by the reaction between a silicon hydride or a siloxane hydride and a platinum (0) or platinum (II) complex (U.S. Pat. No. 4,705,765, Lewis).

Although these platinum complexes and many others are useful as catalysts in processes for accelerating the thermally-activated addition reaction between the compounds containing silicon-bonded hydrogen and compounds containing aliphatic unsaturation, processes for promoting the ultraviolet or visible radiation-activated addition reaction between these compounds may be preferable in some instances. Platinum complexes that can be used to initiate ultraviolet radiation-activated hydrosilation reactions have been disclosed, e.g., platinum azo complexes (U.S. Pat. No. 4,670,531, Eckberg); ($\eta^4$-cyclooctadiene)diarylplatinum complexes (U.S. Pat. No. 4,530,879, Drahnak); and ($\eta^5$-cyclopentadienyl)trialkylplatinum complexes (U.S. Pat. No. 4,510,094, Drahnak). Other compositions that are curable by ultraviolet radiation include those described in U.S. Pat. Nos. 4,640,939 and 4,712,092 and in European Patent Application No. 0238033. U.S. Pat. No. 4,916,169 (Boardman et al) describes hydrosilylation reactions activated by visible radiation. U.S. Pat. No. 6,376,569 (Oxman et al.) describes a process for the actinic radiation-activated addition reaction of a compound containing silicon-bonded hydrogen with a compound containing aliphatic unsaturation, said addition being referred to as hydrosilylation, the improvement comprising using, as a platinum hydrosilylation catalyst, an ($\eta^5$-cyclopentadienyl) tri($\sigma$-aliphatic)platinum complex, and, as a reaction accelerator, a free-radical photoinitiator capable of absorbing actinic radiation, i.e., light having a wavelength ranging from about 200 nm to about 800 nm. The process can also employ, as a sensitizer, a compound that absorbs actinic radiation, and that is capable of transferring energy to the aforementioned platinum complex or platinum complex/free-radical photoinitiator combination, such that the hydrosilylation reaction is initiated upon exposure to actinic radiation. The process is applicable both to the synthesis of low molecular weight compounds and to the curing of high molecular weight compounds, i.e., polymers.

It may be useful to include in the composition additives to improve the working time of the hydrosilylation curable composition. Such hydrosilylation inhibitors are well known in the art and include such compounds as acetylenic alcohols, certain polyolefinic siloxanes, pyridine, acrylonitrile, organic phosphines and phosphites, unsaturated amides, and alkyl maleates. For example, an acetylenic alcohol compound can inhibit certain platinum catalysts and prevent curing from occurring at low temperatures. Upon heating, the composition begins to cure. The amount of catalyst inhibitor can vary up to about 10 times or more of the amount of catalyst, depending upon the activity of the catalyst and the shelf life desired for the composition.

The curable silicone can be at least one free radical-cure silicone comprising a polysiloxane polymer or oligomer having free-radically polymerizable, ethylenically unsaturated groups such as vinyl, allyl, (meth)acryloyl, etc. pendent from the polymer chain and/or the terminal ends. It is desirable for a free radical catalyst to be included for initiating free radical polymerization when the silicone is to be thermally or radiation (e.g., UV or photo) cured. Optionally, a small percentage of a free radically polymerizable vinyl monomer can be included. In addition, a free radically polymerizable cross-linking agent may also be included.

Ethylenically unsaturated free radically polymerizable silicones, including especially the acrylated polysiloxane oligomers and polymers containing terminal and/or pendant ethylenically unsaturated groups, such as acrylate or methacrylate groups, can be prepared by a variety of methods, generally through the reaction of chloro-, silanol-, aminoalkyl-, epoxyalkyl-, hydroxyalkyl-, vinyl-, or silicon hydride-functional polysiloxanes with a corresponding (meth)acryloyl-functional capping agent. These preparations are reviewed in a chapter entitled "Photopolymerizable Silicone Monomers, Oligomers, and Resins" by A. F. Jacobine and S. T. Nakos in Radiation Curing Science and Technology (1992), Plenum: New York, pp. 200-214. Preferred acrylated polysiloxane oligomers include those acryl-modified polydimethylsiloxane resins commercially available from Goldschmidt under the TEGO RC designation and those acrylamido-terminated monofunctional and difunctional polysiloxanes described in U.S. Pat. No. 5,091,483 (Mazurek et al.).

The curable silicone can be at least one condensation-cure silicone. Condensation-curable silicones usually comprise pendent or terminal groups such as, for example, hydroxysilane (i.e., silanol), alkoxysilane or acyloxysilane functional groups that react in the presence of moisture to form cured (i.e., crosslinked) materials. Condensation-curable compositions comprising alkoxysilane or acyloxysilane functionality typically cure in two reactions. In the first reaction, the alkoxysilane or acyloxysilane groups hydrolyze in the presence of moisture and a catalyst to form compounds having silanol groups. In the second reaction, the silanol groups condense with other silanol, alkoxysilane, or acyloxysilane groups in the presence of a catalyst to form —Si—O—Si— linkages. The two reactions occur essentially simultaneously upon generation of the silanol-functional compound. Commonly used catalysts for the two reactions include Bronsted and Lewis acids and are described in the *Encyclopedia of Polymer Science and Engineering,* 2nd Edition, Volume 15, page 252, (1989). A single material may catalyze both reactions.

A variety of approaches have been used for providing condensation-curable compositions that have acceptable cure rates without processing and storage difficulties. For example, U.S. Pat. No. 2,843,555 describes a two-part system, one part comprising a functional polymer and the other part comprising a catalyst with the two parts being mixed just prior before use. U.S. Pat. No. 5,286,815 discloses an ammonium salt catalyst that is inactive until heated sufficiently to liberate an acid compound that initiates the moisture curing reaction. Alternatively, the condensation-curing agent can be a multifunctional cross-linking agent (e.g., an aminosilane) that serves as both catalyst and cross-linker.

U.S. Pat. No. 6,204,350 (Liu et al.), incorporated herein by reference, describes cure-on-demand, moisture-curable compositions of one or more compounds comprising molecules having reactive silane functional groups and an acid generating material are taught therein. The acid generating material releases an acid upon exposure to heat, ultraviolet light, visible light, electron beam irradiation or microwave irradiation to initiate and accelerate the crosslinking reaction.

The curable silicone can be at least one cationic-cure silicone. Cationic-curable silicones usually comprise pendent or terminal groups such as, for example, epoxy, alkenyl ether, oxetane dioxolane, and/or carbonate functional groups that react in the presence of a cationic catalyst to form cured (i.e., crosslinked) materials. If desired, the cationic curable silicone may further comprise a MQ resin to improve the strength of the cured silicone (joining layer).

The epoxysilicones may be prepared by many methods known in the art such as the chloroplatinic acid catalyzed addition reaction of hydride functional silicones with aliphatically unsaturated epoxy compounds, or the epoxidation of vinyl or like unsaturated siloxanes and Grignard type reactions as for example described by E. P. Plueddemann and G. Fanger, J. Am. Chem. Soc. 81, 2632-35 (1959). A convenient method is the hydrosiloxane addition reaction of unsaturated aliphatic epoxy compounds with hydride-functional silicone oligomers. When this method is used, it is preferred that essentially complete reaction of the SiH sites are accomplished although small amounts of hydrogen attached to silicon can be present. It is also preferred for best results that the epoxysilicone is essentially free from low molecular weight components such as cyclic siloxanes, since their presence in the final cured coating could adversely affect the adhesion property of the silicone.

U.S. Pat. No. 5,409,773 (Kessel et al.) describes one or more epoxysilicones having cycloaliphatic and non-cycloaliphatic epoxy groups in a total number which is about 5 to 50% of the total number of siloxane units, the ratio of the total number of cycloaliphatic epoxy groups to the total number of non-cycloaliphatic epoxy groups being from about 1:10 to 2:1, the epoxypolysiloxane(s) being cured in the presence of a catalytically effective amount of a cationic epoxy curing catalyst.

An article entitled "Cationic Photopolymerization of Ambifunctional Monomers" (J. V. Crivello et al., *Macromolekular Symposia*, 95, 79-89, (1995)) describes the photopolymerization of "ambifunctional" monomers (i.e., monomers bearing two chemically different reactive functional groups within the same molecule) using cationic catalysts. In one example, an ambifunctional monomer having both epoxycyclohexyl and trimethoxysilyl reactive functional groups is prepared and then subsequently UV irradiated in the presence of a cationic triarylsulfonium catalyst.

The cured silicone is conveniently obtained by mixing the cationic curable silicone and catalyst and optionally the epoxy-terminated silane in a solvent, coating the solution on the substrate and heating at a suitable curing temperature depending on the effectiveness of the catalyst and heat sensitivity of the substrate. Alternatively, the cationic curable silicone may be cured by means of a photoacid generator, which generates one or more molecules of a Bronsted or Lewis acid on exposure to UV or visible light, and without the application of heat. Mixtures of the epoxypolysiloxanes or mixtures of the epoxysilanes may be used.

Curing of the cationic curable silicone can be effected by mixing with conventional cationic epoxy curing catalysts activated by actinic radiation and/or heat. Catalysts activated by actinic radiation are preferred. Examples of suitable photoinitiators are onium salts of a complex halogen acid, particularly the polyaromatic iodonium and sulfonium complex salts having $SbF_6$, $SbF_5OH$, $PF_6$, $BF_4$, or $AsF_6$ anions, as are disclosed in U.S. Pat. No. 4,101,513, incorporated herein by reference. Preferred photoinitiators are the iodonium and sulfonium salts most preferably having the $SbF_6$ anion. Also useful photoinitiators are organometallic complex salts that are disclosed in U.S. Pat. No. 5,089,536, and supported photoinitiators for the actinic radiation activated polymerization of cationically-polymerizable compounds described in U.S. Pat. No. 4,677,137, both of which are incorporated herein by reference. Suitable heat-activated cationic catalysts which may be used include the heat-activated sulfonic and sulfonylic catalysts described in U.S. Pat. No. 4,313,988, incorporated herein by reference.

The silicone mold of the invention may be prepared by casting a curable silicone resin in a master mold. A patterned master mold is provided bearing the negative of the desired pattern. The master for use with the above described method may be a metallic master, such as nickel, nickel-plated copper or brass, although the master can also be constructed from thermoplastic materials, such as a laminate of polyethylene and polypropylene. One useful master mold is a sheet of thermoplastic resin that is stable to the curing conditions and has been embossed by a metallic master tool such as nickel-plated copper or brass. Such a thermoplastic master is relatively inexpensive and yet can be used to form many patterned absorbent layers before becoming unduly worn.

A partial listing of illustrative methods for generating a master mold with patterned surfaces includes diamond machining (M. A. Davies, C. J. Evans, S. R. Patterson, R. Vohra, and B. C. Bergner, "Application of Precision Diamond Machining to the Manufacture of Micro-photonics Components," Proc. of SPIE 5183 94-108 (2003)), optical lithography, interference lithography, e-beam lithography, x-ray lithography, gray-scale lithography, laser beam writing, electron beam writing, two photon processes, and laser ablation (E. B. Kley, "Continuous Profile Writing by Electron and Optical Lithograph," Microelectronic Engineering 34 261-298 (1997)). Methods for generating a structured surface may include a step where material is exposed to light, X-rays, or electrons and then developed and selectively removed, or a step where a material is etched (Y. Hagiwara, N. Kimura, and K. Emori, U.S. Pat. No. 4,865,954 "Process for Formation of Metallic Relief" (1989)). Material (e.g., metal) can be selectively added onto the substrate surface, to form a structured surface, by convention methods including, for example, sputtering, vapor deposition, and the like. Material (e.g. metal) can be removed from the substrate to form a patterned surface, by convention methods including, for example, etching and the like. These addition and removal methods can be combined with other methods such as, for example, photolithography methods and lift-off methods.

Particularly advantageous approaches for the preparation of a master mold with patterned surfaces include replication or forming a microstructure with a mechanical tool. Mechanical tools form a microstructured surface by embossing, scribing, or molding the microstructure onto the substrate surface. Replication includes the transfer of surface structural feature from a master tool to another material and includes embossing or molding. Methods involving replication are noteworthy for the ease and speed with which materials with structured surfaces can be generated. Also noteworthy is the small size that can be achieved for surface structure features that are generated through replication. Nanoscale features with size less than 10 nanometers, can be replicated (S. R. Quake and A. Scherer, "From Micro- to Nanofabrication with Soft Materials," Science 290 1536-1540 (2000); V. J. Schaeffer and D. Harker, "Surface Replicas for Use in the Electron Microscope," Journal of Applied Physics 13, 427-433 (1942); and H. Zhang and G. M. Bensen, WO 0168940 A1, "Methods for replication, replicated articles, and replication tools" (2001)).

A master mold with patterned surfaces can be prepared through thermal embossing (M. J. Ulsh, M. A. Strobel, D. F. Serino, and J. T. Keller, U.S. Pat. No. 6,0986,247 "Embossed Optical Polymeric Films" (2000); and D. C. Lacey, U.S. Pat. No. 5,932,150 "Replication of Diffraction Images in Oriented Films" (1999)). Thermal embossing involves the pressing of a master mechanical tool against a deformable material, causing the surface structure of the master tool to deform the surface of the deformable material, thereby generating a negative replica of that master tool surface. Materials that can be embossed with surface structure include, for example, soft metals and organic materials such as polymers. Examples of soft metals that can be embossed include indium, silver, gold, and lead. Polymers suitable for thermal embossing include thermoplastics. Examples of thermoplastics include polyolefins, polyacrylates, polyamides, polyimides, polycarbonates, and polyesters. Further examples of thermoplastics include polyethylene, polypropylene, polystyrene poly(methylmethacrylate), polycarbonate of bisphenol A. poly(vinyl chloride), poly(ethylene terephthalate), and poly(vinylidene fluoride). For the preparation of thermally embossed materials, it is often convenient and useful to start with material in film form. Optionally, a film for embossing can include multiple layers (J. Fitch, J. Moritz, S. J. Sargeant, Y. Shimizu, and Y. Nishigaki, U.S. Pat. No. 6,737,170 "Coated Film with Exceptional Embossing Characteristics and Methods for Producing It" (2004); and W. W. Merrill, J. M. Jonza, O. Benson, A. J. Ouderkirk, and M. F. Weber, U.S. Pat. No. 6,788,463, "Post-Formable Multilayer Optical Films and Methods of Forming" (2004)).

Another illustrative method for generating a master mold with patterned surfaces is by scribing. "Scribing" refers to the application of a stylus to an otherwise unstructured surface and pressing or translating the stylus on the surface, generating surface microstructure. A stylus tip may be made of any material such as, for example, a metal, ceramic, or polymer. A stylus tip may include diamond, aluminum oxide, or tungsten carbide. A stylus tip may also include a coating, for example a wear-resistant coating such as titanium nitride.

When preparing a mold of the invention, having nano- and/or micro-size pattern elements, it is desirably prepared from a master mold using techniques including laser ablation mastering, electron beam milling, photolithography, x-ray lithography, machine milling, and scribing.

The pattern of the master mold, and subsequently imparted to the 1st generation negative mold of the invention, and subsequent shaped articles prepared from the 1st generation negative mold, such as $2^{nd}$ generation daughter molds, may be any suitable preselected three-dimensional pattern. The pattern may comprise an array of pattern elements that include, but are not limited to, ridges, channels, mounds, peaks, hemispheres, pyramids, cylinders, cones, blocks, and truncated variations and combinations thereof. The pattern elements may be random or non-random in the x direction, the y direction, or both, with x and y defining the major planar dimensions of the mold. The size of the individual pattern elements may be any suitable size. Generally the individual pattern elements are from about 100 nanometers to 15,000 micrometers, preferably about 100 nanometers to 5000 micrometers in cross section (independently height and width dimensions) and have a repeat distance (i.e. that distance from one element to the next, peak to peak) of 10 nanometers to 15,000 micrometers. The minimal distance between adjacent elements may vary from 0 to 10,000 micrometers. Thus, there may be a flat, unpatterned surface area between adjacent elements, or the elements may be continuous.

When the thermoplastic master mold is made from a radiation-transparent thermoplastic material, a radiation-curable silicone resin can be cured by being irradiated through the master. By using a radiation-transparent master, integral backing layers for the cured sub-master can be opaque. When the master is made from a radiation-transparent thermoplastic resin such as a polyolefin, it is possible to prepare the patterned $1^{st}$ generation silicone mold or other shaped plastic article bearing patterns on both surfaces of the cured silicone layer.

To prepare a $1^{st}$ generation negative mold from a master mold, the silicone resin is added to the master mold to cover the pattern and to fill the voids therein. If the silicone resin precursor is to be thermally or radiation cured, it is desirable to cover the exposed surface with a radiation transparent film or release liner to exclude atmospheric oxygen from the gel precursor, which would tend to interfere with the curing. The silicone resin is added to the mold in amount sufficient to cover the pattern, and achieve the desired thickness and void volume in the product mold.

The silicone mold of the present disclosure comprises an oxidized, patterned surface. Examples of suitable oxidative surface modification techniques include flame treatment, ion beam treatment, electron beam treatment, corona treatment, plasma treatment, electrostatic discharge treatment, light treatment, exposure to reactive gases, and the like (preferably, flame treatment, ion beam treatment, electron beam treatment, corona treatment, plasma treatment, electro static discharge treatment, exposure to reactive gases, and the like; more preferably, flame treatment, ion beam treatment, electron beam treatment, corona treatment, plasma treatment, and the like; most preferably, plasma treatment).

Flame treatment is a method of surface modification wherein active species generated by the combustion reaction in a flame impinge on a surface (for example, on the cured silicone polymer surface), causing oxidation to occur.

Ion beam treatment, or ion sputtering, occurs when atoms are ejected from a target due to ion bombardment. Ion beams (for example, argon-ion beams, argon/oxygen-ion beams, or krypton-ion beams), can be used, for example to clean, oxidize or induce surface roughness on the silicone polymer surface to improve the adhesion of the perfluoro ether silane of formula I.

Electron beam (e-beam) treatment can be used to surface oxidatively modify the patterned, cured silicone polymer. E-beam treatment typically involves the use of concentrated electron fluxes which cause rapid heating, melting, and evaporation of the surface to which the energy is delivered. When the electron flux is removed, the surface rapidly resolidifies. The rapid heating, melting, evaporation, and resolidification cause oxidation and roughening of the surface. E-beam treatment of organic materials typically causes chemical reaction such as, for example, polymerization, crosslinking, chain scission, or degradation.

Corona treatments utilize an atmospheric-pressure alternating current electrical discharge to create active species in a supporting gas that modify the surface chemistry of the silicone polymer surface). Through the use of different gases in the corona, different surface chemistries can be generated. For example, air coronas lead to the oxidation of a polymer surface, nitrogen coronas cause nitrogen affixation to the polymer, nitrogen-hydrogen coronas de-fluorinate fluoropolymers, and helium-fluorocarbon coronas fluorinate surfaces.

Plasma treatment includes plasma induced grafting and surface activation, and reactive ion etching (RIE). Plasma induced grafting uses partially ionized inert gases (for example, argon, neon, krypton, or xenon) to create free radicals on a polymeric surface and generate a reactive and cross-linked surface. Plasma induced surface activation employs a reactive gas to chemically bond functional groups (for example, amine, hydroxyl, carboxyl, carbonyl, or fluorinated groups) to the surface of polymers.

Whereas most surface modification techniques render polymeric and other substrates more wettable (that is, they raise their surface energy), plasma treatment can render surfaces either hydrophobic or hydrophilic. Plasma treatment with inert gases, air, oxygen-containing gases (for example, $O_2$, CO, or $CO_2$), or nitrogen containing gases (for example, $N_2$, $NH_3$, $NO_2$, or NO) typically raises the surface energy of polymeric substrates, making them more hydrophilic. If the gas, however, contains a substantial atom percentage of fluorine (for example, $F_2$, $SF_6$, $CF_4$, $C_4F_8$, $(CF_3)_2O$, $CF_3Cl$, or $CF_3Br$), the surface energy of a polymeric substrate can be substantially lowered, making the surface hydrophobic or even oleophobic (oil repellent). The use of a combined $O_2$/fluorochemical gas plasma is known to impart a low surface coating to surfaces, however, Applicants have found that this technique yields poorer results (limited mold replication) relative the an oxygen plasma with no fluorochemical, followed by treatment with the fluorochemical silane of Formula I. For this reason, oxidizing plasmas preferably contain no fluorochemical.

Reactive ion etching (RIE) involves both sputtering of a surface and chemical reaction. During RIE, the surface to be etched is bombarded with accelerated reactive ions that sputter material off the substrate, as well as react with the substrate material.

Electrostatic charge/discharge treatment can be used to either add charge to a surface or to neutralize/dissipate charge from a surface. Charge, or static electricity buildup, can cause difficulty in wetting or adhering. Electrostatic discharge treatment neutralizes the static buildup by ionizing the surrounding air. Electrically neutral atoms in air are exposed to an applied electric field of voltage to create positively and negatively charged ions. Because of the bipolar nature of the ionized air, the static charge on the material can be neutralized by the oppositely charged ions present in the surrounding air.

Light treatment includes treatment with ultraviolet (UV) light and infrared (IR) light (for example, UV or IR lasers, bulbs, or high powered arc lamps). UV light can be used, for example, to induce crosslinking in a polymer film and render exposed areas insoluble. UV light can photodegrade some polymers, however. This degradation can be avoided or minimized by using thermal irradiation/local heating with low energy IR light.

Exposure to reactive gases can effect surface modification of some substrates. For example, exposing a hydrogen-terminated silicon surface to a halogenated gas (for example, a chlorinated gas) can result in a halogen-terminated (for example, chlorine-terminated) silicon surface (see, for example, U.S. Pat. No. 6,403,382 (Zhu et al.)). The chlorine-terminated areas of the silicon surface are significantly more reactive than the hydrogen-terminated areas.

Another alternative is ozone treatment or the combined exposure of ozone and UV light, particularly at wavelengths from 200-300 nm. These surface treatments can also be applied using an in-line system or method that includes another film processing step(s) after the surface treatment, such as adhesive coating and lamination to other optical films.

The silicone mold of the instant disclosure comprises a release coating of the fluorochemical silane of Formula I on the oxidized, patterned surface. A release coating of may comprise a self-assembled monolayer of the compound of Formula I on the oxidized, patterned surface of the silicone mold (i.e., a fluorine-containing polyorganosiloxane film), As used herein, "self-assembled" refers to spontaneous adsorption of the active coating ingredient to the oxidized, patterned surface of the silicone mold. In embodiments of replicating micro- or nano-sized pattern elements, the overall coating thickness of the release coating (which is believed to be covalently bonded to the oxidized silicone surface through siloxane linkages) is equal to or greater than a monolayer, which is typically less than about 50 Angstroms thick and greater than about 15 Angstroms thick. The release coating may be at least about 15 Angstroms thick, or at least about 30 Angstroms thick. Preferably, it is less than about 100 Angstroms thick, and more preferably, less than about 50 Angstroms thick for pattern elements or features of less than 500 nanometers. Larger sized patterned elements or features may accommodate thicker coatings without deleteriously affecting the replication fidelity. Applicants have verified the formation of a self-assembled monolayer of a compound of Formula I on a silicon wafer of approximately 20 Angstroms by ellipsometric analysis, under the same conditions used to treat the oxidized silicone molds.

In other embodiments of replicating larger pattern features, or in embodiments where precise replication if not necessary, coating thicker coatings may be desirable, e.g. greater than 100 Angstroms, in which a monolayer base film is adsorbed or associated with additional siloxane derived from hydrolysis and condensation of the silane of Formula I, which is believed to be relatively low molecular weight oligomeric fluorinated siloxane material (i.e., fluorine-containing polyorganosiloxane material having other heteroatoms and/or functional groups) that is loosely bound to the monolayer base film. This oligomeric material can be of varying thickness, depending on process conditions, and can be readily removed by rinsing with an organic solvent.

The release coating of Formula I can be applied to the oxidized, patterned silicone mold by a variety of techniques. Preferably, the oxidized, patterned silicone mold is treated with a coating composition (typically, a solution) comprising a fluorinated silane of Formula I. All surfaces or a portion of only one surface of the mold may be treated, although advantageously the entire patterned surface is coated. Although a wide variety of treatment modes can be used, such as spraying, casting, rolling, or immersing, a preferred treatment mode is to immerse the mold in the coating composition. This method preferably reduces solvent emissions and opportunities for damaging the mold. The coating composition is typically a relatively dilute solution, preferably containing less than about 2.0 weight percent of the fluorinated silane, more preferably, less than about 0.5 weight percent of the fluorinated silane, and most preferably, less than about 0.3 weight percent of the fluorinated silane. Useful solvents include any solvent in which the perfluoroether silane is soluble, is non-reactive to either the silane of silicone. Preferably the solvent is selected from fluorinated solvents, including partially and perfluorinated solvents. Most preferable solvents include hydrofluorother solvents, such are described in US 20050048288A1 (Flynn et al.)

The mold to be coated is typically contacted with the coating composition (typically, a coating solution) at room temperature (i.e., about 20° C. to about 25° C.) for a relatively short period of time. After a short period of time in contact with the coating composition (as by immersing), the substrate is withdrawn. Typically, the contact time (i.e., the total time the mold is in contact with the coating composition) is less than about 30 minutes. Preferably, the contact time is less than about 20 minutes, more preferably, less than about 10 minutes, and most preferably, less than about 5 minutes.

For certain embodiments a subsequent heat treating step may be beneficial. Although in some embodiments, a stream of nitrogen or dry air may be needed to remove a slight excess of coating composition, preferably, there is no adhering film or droplets of excess coating composition on the mold upon removal from the coating composition. The absence of excess coating composition on the mold is enhanced by using a sufficiently clean substrate and removing the substrate from the coating composition at a sufficiently slow rate (typically, at a rate of about 0.1 centimeter/second to about 2.5 centimeters/second, and preferably, at a rate of about 0.5 centimeter/second).

Shaped plastic articles, such as second generation daughter molds, are typically prepared by pouring or filling silicone $1^{st}$ generation negative mold (having an oxidized, patterned surface and a layer of the fluorochemical silane release agent of Formula I) with curable silicone resin composition, curing the same, and removing from said mold master the resulting in a second generation daughter mold (or other shaped silicone articles) which comprises cured silicone resin and has a surface bearing microstructure replicated from the mold master. The silicone resin is selected from the curable silicones previously described, and may be the same or different from that of the $1^{st}$ generation negative silicone mold.

The viscosity of the uncured silicone resin composition should be within the range of about 1,000 to 5,000 cps. Above that range, air bubbles might be entrapped, and the resin might not completely fill the cavities of the master. If an attempt were made to obtain a viscosity below that range, the overall equivalent weight (weight per number of reactive groups) of the uncured silicone resin typically would be so low that the resin would experience shrinkage upon curing to such an extent that the cured silicone resin would not faithfully replicate the master molding surface. Preferably, the viscosity of the resin is from 2,000 to 3,000 cps. Within that preferred range, the silicone resin composition should completely fill the cavities without any need to apply more than hand pressure. However, when the cavities are unusually deep and/or narrow, it may be desirable to reduce the viscosity below about 2,000 cps, because some shrinkage is to be preferred over any failure to fill the cavities completely.

For cube-corner sheeting, linear Fresnel lenses, and other shaped plastic articles having raised or indented microstructure-bearing surfaces, mold masters can be used which are made of plastic, e.g., acrylonitrile-butadienestyrene, or preferably (for mass production of such replicated articles) made of metal fabricated directly from a suitable metal by engraving, hobbing, assembling as a bundle a plurality of metal parts machined in the desired configuration, or other mechanical means or by electroforming, e.g., see "Encyclopedia of Polymer Science & Technology", Vol. 8, p. 651 (1968), and "Principles of Electroplating and Electroforming", W. Blum and G. B. Hogaboom, 3rd Ed. McGraw-Hill Co., Inc., Chap. VIII (1949), and U.S. Pat. No. 3,689,346.

Following curing of the cast silicone resin, the cured, shaped plastic article is readily separated or removed from the mold master. Depending on the particular shaped plastic article made and the nature of the mold master, the mold master can be repeatedly used for replication done on a continuous mass production basis.

EXAMPLES

Example 1 a) Process for Fabrication of the Master Mold

An anti-reflective coating (ARC UV-112, available from Brewer Science, Rolla, Mo.) was applied to the surface of a Si wafer (available from Montco Silicon Technologies, Inc., Spring City, Pa.) before applying a photoresist, in order to avoid degradation of the pattern due to reflected light. A 15 μm thick layer of SU-8 photoresist (available from Micro-Chem Corp., Newton, Mass.) was coated onto the ARC-coated Si wafer by spin coating, followed by baking at a temperature of 65° C. for 2 min and then 95° C. for 2 min.

The SU-8 photoresist (a negative photoresist commercially available from Micro-Chem Inc. of Santa Clara, Calif.) was exposed using a conventional photolithography system (obtained from Neutronix Quintal Corp., Morgan Hill, Calif.) in order to obtain post and hole structures. After the exposure, a post-exposure bake (PEB) at 65° C. for 2 min and then 95° C. for 2 min was performed to selectively cross-link the exposed portions of SU-8 photoresist. The SU-8 was then developed in propylene glycol methyl ether acetate (PGMEA, available from MicroChem Corp., Newton, Mass.) and treated with a fluorinated silane release agent before the next step of polydimethylsiloxane (PDMS) replication.

SEM images of SU-8 post and hole structures revealed the post diameter is about 7.2 μm, the post height is about 15 μm, and the pitch is 11 μm. The hole diameter is 7.5 μm, its depth is about 15 μm, and the pitch is 11 μm.

b) Silicone $1^{st}$ Generation Negative Mold Made from the SU-8 Photoresist Master Structure of Step a Poly(dimethylsiloxane) (PDMS) and its curing agent (available as SYLGARD 184 Silicone Elastomer Kit, available from Dow Corning, Midland, Mich.) were thoroughly mixed in a 10:1 weight ratio. Air bubbles trapped in the mixture were removed by degassing for 30 min at low vacuum. The degassed mixture was poured onto the patterned SU-8 (from part a), further degassed for another 30 min, and then cured on a hot plate at 80° C. for 1 h. After the curing, the silicone negative mold was peeled off the SU-8 master, yielding the desired silicone $1^{st}$ generation negative mold with negative structures.

Before coating the perfluoroether silane release agent on the silicone $1^{st}$ generation negative mold, an oxygen plasma treatment of the mold was carried out by using a reactive ion etching (RIE) system (The RIE was done using a Model PLASMA LAB System 100, available from Oxford Instruments, Yatton, UK.) in order to generate a silanol group (Si—OH) on the mold surface. It is believed this treatment allows the release agent to chemically bond to the mold surface, resulting in a self-assembled monolayer (SAM) as an anti-adhesion layer on the mold to allow further replication. The parameters used for $O_2$ plasma treatment of the mold are as follows:

| | |
|---|---|
| RF power: | 200 W |
| Pressure: | 10 mTorr |
| ICP power: | 1500 W |
| $O_2$: | 20 sccm |
| Time: | 8 s |

Following the plasma treatment, the 1st generation negative mold (having a post and hole patterned surface) was coated with a release agent of the formula where c is about 5.

The perfluoropolyether silane was prepared from "HFPO methyl ester" —$C_3F_7O(CF(CF_3)CF_2O)_cCF(CF_3)C(O)OCH_3$, wherein "c" averages about 5, according to the method of U.S. Pat. No. 3,250,808 (Moore et al.), with purification by fractional distillation. A 4 oz screw-cap bottle was charged with 108.2 g HFPO methyl ester and 18.38 g 3-aminopropyltrimethoxysilane. The bottle was capped and shaken, and the initially cloudy mixture warmed and clarified within a few minutes. The mixture was allowed to stand at room temperature for several days, at which time analysis by infrared spectroscopy indicated complete conversion of ester to amide. The product, perfluoropolyether silane, was used without additional purification.

The 1st generation negative mold was coated by dip coat in 0.1 wt % solution of the release agent in HFE-7100™ hydrofluoroether solvent (available from the 3M Company). The coated mold was heated for 1 hr at 120° C., then cooled and rinsed for 1 min in fresh HFE-7100™. After this treatment, the mold is ready for use in the replication process.

c) Silicone 2nd Generation Daughter Mold Made from Silicone 1st Generation Negative Mold Produced in Step b De-gassed Sylgard 184 silicone mixture (described above) was poured on the silicone 1st generation negative mold, further degassed for another 30 min, and then cured on a hot plate at 80° C. for 1 hr. After curing, the silicone 2nd generation daughter mold was easily peeled off the silicone 1st generation negative mold.

Figure 1:
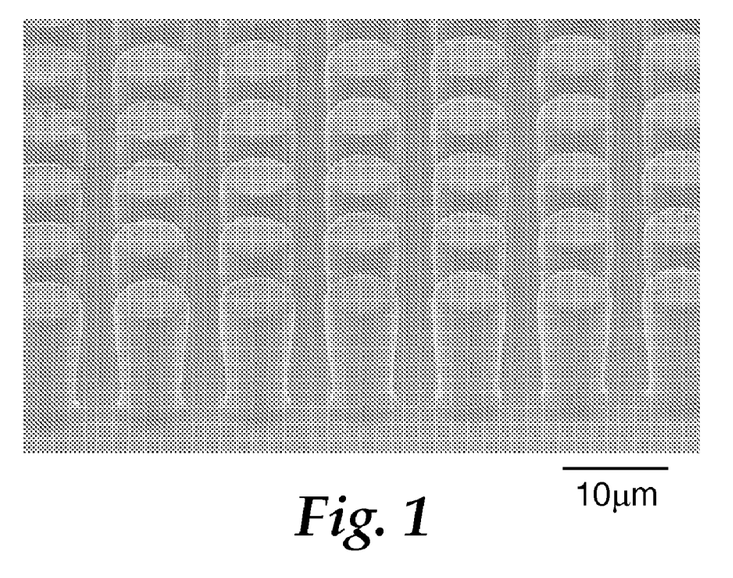
FIGS. 1 and 2 are digital images of scanning electron micrographs of the $2^{nd}$ generation daughter mold of Example 1.
Figure 2:
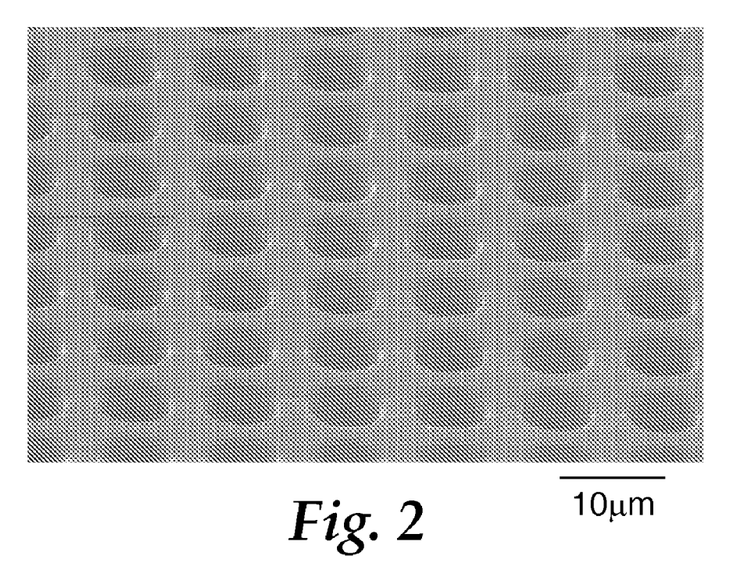

FIGS. 1 and 2 show the silicone 2nd generation daughter mold with post structures and hole structures made from the silicone 1st generation negative mold (step b). As can be seen, the replicated post) and hole structures in the silicone 2nd generation daughter mold are slightly smaller than the corresponding features of the SU-8 masters:

|  | Post diameter | Hole diameter |
|---|---|---|
| SU-8 1st generation mold | 7.2 μm | 7.5 μm |
| 2nd generation daughter mold | 6.4 μm | 6.5 μm |

Example 2

Replication of a Master Photoresist Pattern Having Small Features

A microlens array mold having a microlenses size of approximately 300 nanometers were made by interference lithography using a 244 nm frequency doubled argon laser with an output of 300 mW (Sabre FreD Laser, available from Coherent Inc., Santa Clara, Calif.) in a positive photoresist (Shipley UV5 resist, available from Rohm and Haas Electronic Materials Inc., Marlborough, Mass.).

The Sylgard 184™ silicone mixture was degassed and was poured on the photoresist master and further degassed for another 30 min, and then cured on a hot plate at 80° C. for 1 hr. After curing, the silicone 1st generation negative mold was easily peeled off the photoresist master. The silicone 1st generation negative mold was oxidized by treating with $O_2$ plasma and then coated with release agent as in example 1.

Sylgard 184™ silicone mixture was degassed and was poured on the silicone 1st generation negative mold and further degassed for another 30 min, and then cured on a hot plate at 80° C. for 1 hr. After the curing, the silicone 2nd generation daughter mold was peeled off the silicone 1st generation negative mold.

Figure 3:
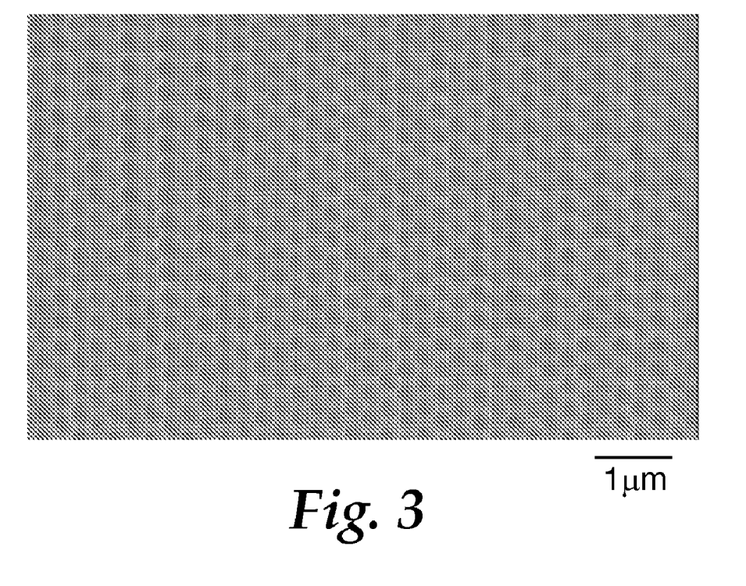
FIGS. 3 and 4 are digital images of scanning electron micrographs of the $2^{nd}$ generation daughter mold of Example 2.
Figure 4:
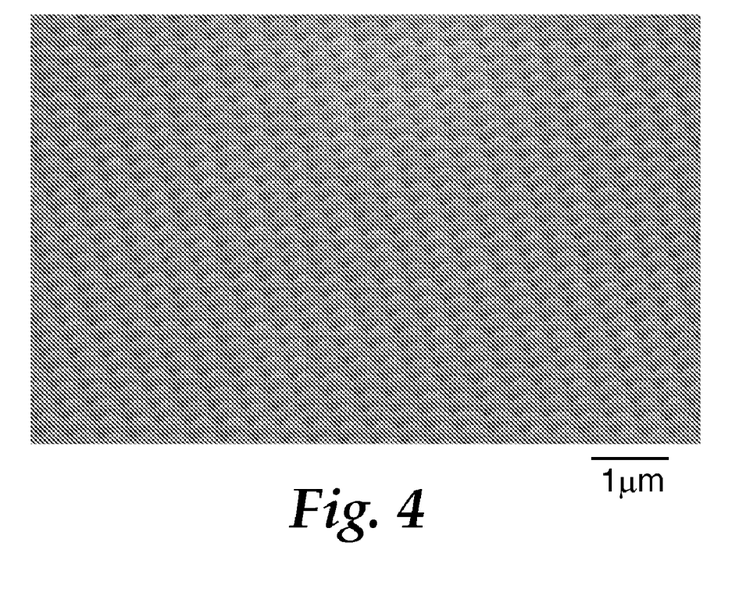

FIGS. 3 and 4 show the silicone 2nd generation daughter mold with post structures made from the silicone 1st generation negative mold. As can be seen, the post structures between the PR master and the silicone 2nd generation daughter mold are very similar, demonstrating clearly that feature sizes as small as 330 nm can be replicated with this approach.

Comparative Example 1

The silicone 1st generation negative mold for the comparative example 1 was made as the same as in Example 1, which was then treated by heating at 150° C. for 30 min. No oxidizing treatment or release coating was used.

Comparative Example 2

The silicone 1st generation negative mold was prepared as in Example 1. The silicone 1st generation negative mold was treated by $O_2$ plasma and following $C_4F_8$ plasma to form fluoropolymer on the mold.

Table 1 shows the comparison of replication results for Example 1, and Comparative Examples 1 and 2.

TABLE 1

| Example | Treatment | Failure of separating the silicone replica from the silicone 1st generation negative mold |
|---|---|---|
| Comparative 1 | Thermal | First replica poor |
| Comparative 2 | $O_2$ plasma + $C_4F_8$ plasma | 3-5 time replicas before poor replication |
| Example 1 | $O_2$ plasma + release agent | No failure over 10 replicas |

The invention claimed is:

1. A silicone mold comprising an oxidized, patterned surface, and a layer of perfluoroether silane release agent on the patterned surface, said release agent is of the formula:

$$R_f-[-R^1-Si(Y)_{3-x}(R^2)_x]_y \quad (I)$$

wherein:
$R_f$ is a monovalent or divalent perfluoroether group;
$R^1$ is a divalent alkylene group, arylene group, or combinations thereof, optionally containing one or more heteroatoms or functional groups and optionally substituted with halides, and preferably containing about 2 to about 16 carbon atoms;
$R^2$ is a lower alkyl group,
Y is a hydrolysable group;
x is 0 or 1; and y is 1 or 2.

2. The mold of claim 1, wherein $R^1$ is of the formula:

—$R^4$-Q-$R^5$—, wherein $R^4$ and $R^5$ are each independently a covalent bond, —O—, or a divalent alkylene or arylene group, or combinations thereof, said alkylene groups optionally containing one or more catenary oxygen atoms;

Q is $-CO_2-$, $-SO_3-$, $-CONR^6-$, $-O-$, $-S-$, a covalent bond, $-SO_2NR^6-$, or $-NR^6-$, wherein $R^6$ is hydrogen or $C_1-C_4$ alkyl.

3. The mold of claim 1, wherein $R_f$ is a perfluoroether group comprising perfluorinated repeating units selected from the group consisting of
$(C_nF_{2n}O)-$, $-(CF(Z)O)-$, $-(CF(Z)C_nF_{2n}O)-$, $-C_nF_{2n}CF(Z)O)-$, $-(CF_2CF(Z)O)-$, and combinations thereof, wherein n is 1 to 6 and Z is a perfluoroalkyl group, a perfluoroalkoxy group, or perfluoroether group.

4. The mold of claim 1, wherein said perfluoroether moiety of said perfluoroether release agent is selected from:
$-CF_2O(CF_2O)_a(C_2F_4O)_bCF_2-$; $-CF_2O(C_2F_4O)_bCF_2-$, $-CF(CF_3)O-(CF_2CF(CF_3)O)_c-C_nF_{2n}O-(CF(CF_3)CF_2O)_c-CF(CF_3)-$, and $-(CF_2)_3O(C_4F_8O)_d(CF_2)_3-$, wherein each of a, b, c and d may be zero, and a+b+c+d is at least 1, and n is 1 to 6.

5. The mold of claim 1, wherein $R_f$ is a monovalent perfluoroether group.

6. The mold of claim 1 wherein the oxidized, patterned silicone mold surface comprises a flame treated-, ion beam treated-, electron beam treated-, corona treated-, plasma treated-, electrostatic discharge treated-, and light treated- patterned silicone surface.

7. The mold of claim 1 wherein the release agent comprises a self-assembled monolayer (SAM).

8. The mold of claim 1 wherein said silicone mold comprises a cured silicone selected from addition curable silicones, condensation curable silicones, free-radical curable silicones, and cationic curable silicones.

9. The mold of claim 1 wherein the pattern elements of said oxidized, patterned surface are 100 nanometers to 15,000 micrometers in cross section and have a repeat distance of 10 nanometers to 15,000 micrometers.

10. The mold of claim 1, wherein said layer of perfluoroether silane is less than 100 Angstroms in thickness.

11. A method of replication comprising:
providing the mold of claim 1,
adding an uncured silicone resin in contact with the oxidized, patterned surface of said mold;
curing the silicone resin, and separating the cured silicone resin from the mold.

12. The method of claim 11 wherein said uncured silicone resin is selected from addition curable silicones, condensation curable silicones, free-radical curable silicones, and cationic curable silicones.

13. The method of claim 11, where said replication is repeated at least ten times.

14. The method of claim 11 wherein the uncured silicone resin is different than the silicone of the mold of claim 1.

15. A method for preparing the mold of claim 1 comprising the steps of
1. providing a master mold,
2. contacting the master mold with a curable silicone,
3. curing,
4. removing the cured silicone mold having a pattern on the surface thereof,
5. oxidizing the patterned surface;
6. contacting the patterned surface with said perfluoroether silane release agent.

16. The method of claim 15 wherein the step of oxidizing the patterned silicone mold surface comprises a flame treating, ion beam treating, electron beam treating, corona treating, plasma treating, electrostatic discharge treating, and light treating.

17. The method of claim 15 wherein said step of contacting comprises solution coating.

18. The method of claim 15 wherein said step of contacting provides a coating of said perfluoroether silane of less than 100 Angstroms thickness.

19. The method of claim 15 further comprising the step of heating after contacting the patterned surface with said perfluoroether silane release agent.

* * * * *

UNITED STATES PATENT AND TRADEMARK OFFICE
CERTIFICATE OF CORRECTION

| | | |
|---|---|---|
| PATENT NO. | : 7,891,636 B2 | |
| APPLICATION NO. | : 11/845465 | |
| DATED | : February 22, 2011 | |
| INVENTOR(S) | : Jun-Ying Zhang | |

It is certified that error appears in the above-identified patent and that said Letters Patent is hereby corrected as shown below:

On the title page, item [56]
Page 2, Column 2,
Under "Other Publications", Line 41, delete "INSM" and insert -- ISNM --.
Under "Other Publications", Line 52, delete "Wacher-Chemie," and insert -- Wacker-Chemie, --.

Column 4,
Line 18, delete "e.g" and insert -- e.g. --.
Line 57, delete "($CnF_{2n}$)" and insert -- ($C_nF_{2n}$) --.

Column 5,
Line 11, delete "($X'C_nF_{2+1}$)" and insert -- ($X'C_nF_{2n+1}$) --.
Line 41, delete "formula 1" and insert -- formula I --.
Line 65, delete "$R^1$" and insert -- R --.

Column 7,
Line 15-16, delete "—$CH_2$—O($CH_2$)$_3$—," and insert -- —$CH_2O(CH_2)_3$—, --.

Column 11,
Line 46-47, delete "Macromolekular" and insert -- Macromolecular --.

Column 16,
Line 63, delete "hydrofluorother" and insert -- hydrofluoroether --.

Column 20,
Line 65, delete "—$R^4$-Q-$R^5$—, wherein" and insert -- —$R^4$—Q—$R^5$—, wherein --.

Column 21,
Line 10, delete "—$C_nF_{2n}CF(Z)O)$—," and insert -- —($C_nF_{2n}CF(Z)O$)—, --.

Signed and Sealed this
Twenty-sixth Day of July, 2011

David J. Kappos
*Director of the United States Patent and Trademark Office*